(12) United States Patent
Jens et al.

(10) Patent No.: US 6,613,851 B1
(45) Date of Patent: Sep. 2, 2003

(54) CATALYST FOR THE POLYMERIZATION OF OLEFINS

(75) Inventors: Klaus-Joachim Jens, Langesund (NO); Mats Tilset, Bekkestua (NO); Mark H Voges, Leverkosen (DE); Richard Blom, Oslo (NO); Morten Frøseth, Oslo (NO)

(73) Assignee: Borealis Technology Oy, Porvoo (FI)

( * ) Notice: Subject to any disclaimer, the term of this patent is extended or adjusted under 35 U.S.C. 154(b) by 0 days.

(21) Appl. No.: 09/720,650

(22) PCT Filed: Jun. 23, 1999

(86) PCT No.: PCT/GB99/01962

§ 371 (c)(1),
(2), (4) Date: Mar. 26, 2001

(87) PCT Pub. No.: WO00/01739

PCT Pub. Date: Jan. 13, 2000

(30) Foreign Application Priority Data

Jul. 1, 1998 (GB) .............................................. 9814282

(51) Int. Cl.⁷ ............................ C08F 4/64; C08F 4/642; C08F 4/68; C08F 4/69
(52) U.S. Cl. ........................ 526/160; 526/169; 526/161; 526/172; 526/126; 526/348; 526/943; 502/117; 502/103; 502/155; 502/167

(58) Field of Search ................................. 526/160, 169, 526/161, 172, 126, 348, 943; 502/117, 103, 155, 167

(56) References Cited

U.S. PATENT DOCUMENTS 5,705,619 A * 1/1998 Herrmann .................... 534/10

FOREIGN PATENT DOCUMENTS

WO    WO 97 34875 a    9/1997

OTHER PUBLICATIONS

Grubbs, Robert H. et al, "Metal carbene complexes in polymer synthesis", Nato Asi Ser., Ser. C (1987), 215 (Recent Adv. Mech. Synth. Aspects Polym.), 343–52.

Voges, Mark H. et al, "Synthesis and Characterization of 14–Electron Cyclopentadienyl Chromium(II) Complexes Containing a Heterocyclic Carbene Ligand", Organometallics (1999), 184(4), 529–533, Feb. 15, 1999.

* cited by examiner

Primary Examiner—David W. Wu
Assistant Examiner—R. Rabago
(74) Attorney, Agent, or Firm—Nixon & Vanderhye

(57) ABSTRACT

The invention relates to the use of cyclic carbene-η-ligand complexes for catalysis of olefin polymerization.

23 Claims, No Drawings

CATALYST FOR THE POLYMERIZATION OF OLEFINS

This invention relates to novel catalysts and their use in polyolefin production, in particular to cyclic-carbene-η-ligand catalysts useful in the preparation of polyolefins, in particular polymers of $C_{2-8}$ olefins, more especially polypropylenes and most especially polyethenes.

Polyolefins of superior mechanical and processing properties may be obtained if the molecular-weight distribution is tailored to the end use of the polymer. Traditional olefin polymerization catalysts, such as chromium on silica, produce polyethylenes with a wide molecular weight distribution. Such materials are well suited for making moulded products. However, these moulded products would be significantly improved if it were possible to produce a polymer containing a tailored molecular weight distribution combined with controlled insertion of comonomer into the desired part of the molecular weight distribution.

One solution to this problem is to produce the olefin polymer using two or more metallocene complex catalysts simultaneously. Typically, combinations of zirconocene complexes have been disclosed. However, while zirconocene dichloride is useful to produce the low molecular weight fraction of a polymer, no satisfactory comonomer control is achieved, ie. branched polyolefin chains are produced in the presence of a mixed olefin feedstock (for example ethylene-hexene) This is generally true for the overwhelming majority of the known metallocene complexes.

It is therefore desirable to identify an olefin polymerization catalyst exhibiting comonomer control, ie. which will not build certain comonomers into the growing polymer chain even though such comonomers are present in the polymerisation feedstock.

It is an object of the invention to provide such a catalyst system.

Thus viewed from one aspect the invention provides a process for the catalysed polymerization of a an olefin, especially a $C_{2-8}$ α-olefin, preferably a $C_2$ or $C_3$ α-olefin, more preferably ethene, characterised in that as a catalyst or catalyst precursor is used a cyclic carbene-η-ligand complex comprising a catalytically effective coordinated metal, preferably a group 6 metal, and more especially chromium.

Viewed from a further aspect the invention provides an olefin polymerization catalyst or catalyst precursor comprising a cyclic carbene-η-ligand complex comprising a catalytically effective coordinated metal, preferably a group 6 metal, and more especially chromium.

In the cyclic carbene-η-ligand complex, the cyclic carbene ligand may be any cyclic carbene capable of coordinating to the metal. Typically the carbene is heterocyclic with the C: providing one ring atom, and especially preferably with the ring unsaturated. In general, the atoms adjacent the C: will be substituted, preferably with bulky substituents containing up to 30 non-hydrogen atoms, preferably at least 4 non-hydrogens e.g. containing 4 to 12 carbon atoms. Moreover the substituent itself may comprise a further carbene structure. More preferably, the carbene comprises a 5 membered, preferably mono-unsaturated, heterocyclic ring which contains 2, 3 or 4 ring nitrogens, two of which are optionally substituted and 1, 2 or 3 ring carbons one of which (the C: atom) is adjacent at least one ring nitrogen and is unsubstituted with any remaining ring carbon optionally being substituted. Thus for example the carbene may be of formula Ia or Ib

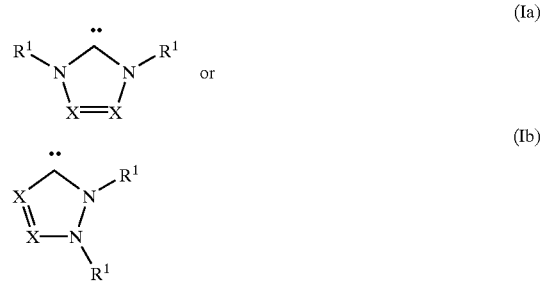

where each X may independently represent N or an optionally substituted CH group; and each $R^1$ is hydrogen, or an optionally substituted organic group.

Carbenes of formula Ia, especially where the $R^1$ groups are bulky substituents and more especially where the ring atoms of each X are carbon, are particularly preferred.

The carbenes of formula Ia or Ib are sometimes referred to as Arduengo carbenes (as opposed to the Fischer and Schrock carbenes which are more commonly encountered in publications relating to organometallic complexes). The Arduengo carbenes tend to be more stable—if they dissociate from a metal complex they usually have sufficiently large half lives to re-enter the metal's coordination sphere. Such stability facilitates the synthesis of substituted derivatives allowing greater freedom to modify the electronic and steric properties of the carbene. The Arduengo carbenes moreover tend to bind efficiently to metals whether in low or high oxidation states as opposed to Fischer and Schrock carbenes which favour low and high oxidation states respectively; this is advantageous in polymerization catalysis where oxidation state changes may occur. The Arduengo carbenes are efficient 2-electron donor ligands (comparable to $P(CH_3)_3$ or $P(C_6H_{11})_3$) with no tendency to act as Π acceptors—again in contrast to Fischer and Schrock carbenes—and may be used in place of phosphine ligands.

The strong metal:Arduengo carbene bond strengths (comparable to or greater than metal:phosphine bond strengths) mean that the complexes are thermally robust. Accordingly such carbenes have good catalyst lifetimes and thermal stabilities.

Many such carbenes of formulae Ia or Ib are already known as ligands, e.g. compounds having the following skeletal structures (ie. omitting ring substituents):

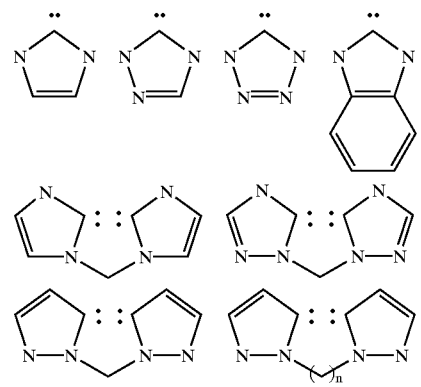

-continued

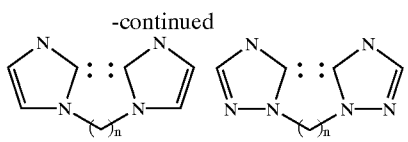

(where n is from 1 to 6).

The range of substituents the carbene ring nitrogens and ring carbons may carry is very large, with different substitution patterns resulting in variations in the properties of the resulting catalyst.

Thus for example substituents may be selected from halogen atoms, non-carbon oxyacid groups and derivatives thereof, and optionally substituted alkyl, aralkyl and aryl groups, e.g. such groups substituted by groups selected from alkyl, aryl, amino, hydroxy, alkoxy, oxo, oxa, carboxy, thia, sulphur oxyacid and halo groups and combinations thereof. Examples of particular ring substituents include for example methyl, ethyl, i-propyl, t-butyl, n-butyl, n-hexyl, cyclohexyl, phenyl, hydroxyphenyl, optionally substituted ferrocenyl (e.g. $(C_5H_4)Fe(C_5H_5)$), benzyl, methylbenzyl, 1-phenyl-ethyl, mesityl, methylnaphthyl, ethoxyethyl, diphenylmethyl, ethylaminoethyl, diethylamino-methyl, 2-(diethylamino)-ethyl, 2-carboxy-ethyl, 2-sulphoxy-ethyl, 4-sulphoxy-butyl, 2-ethoxycarbonyl-ethyl, chlorophenyl, adamantyl, dihydroimidazol-ylidinylmethyl, dihydropyrazolylidinylmethyl, 2,6-diisopropylphenyl, or dihydrotriazolylidinylmethyl groups.

Particular examples of suitable carbenes include compounds of formulae IIa to IIj

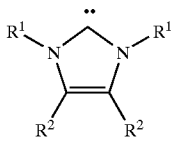
(IIa)

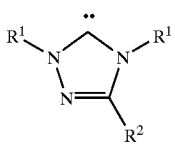
(IIb)

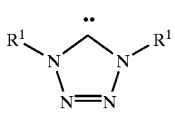
(IIc)

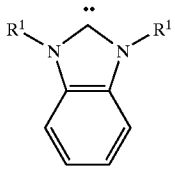
(IId)

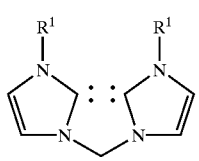
(IIe)

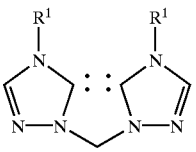
(IIf)

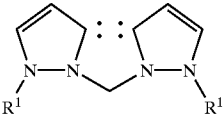
(IIg)

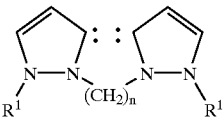
(IIh)

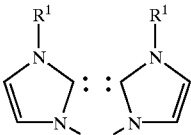
(IIi)

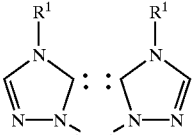
(IIj)

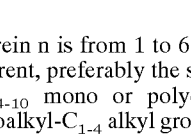

wherein n is from 1 to 6 and each $R^1$, which is the same or different, preferably the same, represents a $C_{1-6}$ alkyl group, a $C_{4-10}$ mono or polycyclic cycloalkyl group, a $C_{4-10}$ cycloalkyl-$C_{1-4}$ alkyl group, an aryl group, an aryl-$C_{1-4}$ alkyl group, a $C_{1-6}$ alkyl-aryl-$C_{1-4}$ alkyl group, a carboxy group or derivative thereof (e.g. an ester group), or a ferrocenyl group, in which any alkyl, alkylene, aryl or arylene moiety is optionally substituted, e.g. with amino, hydroxy, alkoxy, halo, nitro, cyano, oxyacid (e.g. carbon oxyacid or sulphur oxyacid) or oxyacid derivative (thus by way of example $R^1$ might represent 2-hydroxy-phenyl); and $R^2$ which may be the same or different is hydrogen, halogen, $C_{1-6}$ alkyl or an aryl group or two $R^2$ groups on adjacent carbons can together form an optionally substituted carbocyclic group, e.g. a 5 to 7 membered ring.

Unless otherwise specified, alkyl groups or alkylene moieties referred to herein may conveniently contain 1 to 10, more preferably 1 to 6 carbons and are linear or branched. Likewise unless otherwise specified aryl groups are preferably homo or heterocyclic containing 5 to 7 ring atoms per ring and with such rings containing 0, 1, 2, 3 or 4 ring heteroatoms selected from 0, N and S, preferably 0, 1, 2 or 3 N atoms, and with the groups containing a total of 5 to 16 ring atoms. The ring atoms may be substituted, e.g. by alkyl groups and other groups listed above or by fused saturated or unsaturated rings. Examples of typical aryl groups include phenyl, naphthyl, mesityl, 2,6-diisopropyl-phenyl, 2,6-ditertbutyl-phenyl, and 2,6-ditertbutyl-4-methylphenyl.

Examples of suitable carbenenes and carbene-metal complexes and procedures for their synthesis are described in the literature, e.g. in öfele, K. J. *Organomet. Chem.*, 1968,12, 42–43; Wanzlick, H. W. et al., *Angew. Chem., Int. Ed. Engl.* 1968, 7, 141–142; öfele, K. et al., *Angew. Chem., Int. Ed. Engl.* 1970, 9,739–740; Schönherr, H. J. et al., *Chem. Ber.* 1970, 103, 1037–1046; Schönherr, H. J. et al., *Liebigs Ann.*

Chem. 1970, 731, 176–179; Luger, P. et al., *Acta Cryst., Sect. B* 1971, B27, 2276–2279; öfele K. et al., *Chem. Ber.* 1972, 105, 529–540; öfele, K. et al., *Z. Naturforsch.* 1973, 28B, 306–309; Kreiter, C. G. et al., *Chem. Ber.* 1976, 109, 1749–1758; öfele, K. et al., *Z. Naturforsch.* 1976, 31B, 1070–1077; Krist, H. G. Dissertation, Technische Universität München, 1986; Bonati, F. et al., *J. Organomet. Chem.* 1989, 375, 147–160; Arduengo, A. J., III et al., *J Am. Chem. Soc.* 1991, 113, 361–363; Bonati, F. et al., *J Organomet. Chem.* 1991, 408, 271–280; Arduengo, A. J., III et al., *J Am. Chem. Soc.* 1992, 114, 5530–5534; Herrmann, W. A. et al., *Chem. Ber.* 1992, 125, 1795–1799; Britten, I. F. et al., *Acta Cryst., Sect. C* 1992, C48, 1600–1603; Mihailos, D. Dissertation, Technische Universität München, 1992; Arduengo, A. I., III et al., *Organometallics* 1993, 12, 3405–3409; Arduengo, A. I. et al., *J Organomet. Chem.* 1993, 462, 13–18; Öfele, K. et al., *J Organomet. Chem.* 1993, 459, 177–184; Kuhn, N. et al., *Synthesis* 1993, 561–562; Arduengo, A. I., III et al., *J Am. Chem. Soc.* 1994, 116, 4391–4394; Arduengo, A. I., III. et al., *J Am. Chem. Soc.* 1994, 116, 7927–7928; Schumann, H. et al., *Angew. Chem., Int. Ed. Engl.* 1994, 33, 1733–1734; Kuhn, N. et al., *J Organomet. Chem.* 1994, 470, C8–C11; Herrmann, W. A. et al., *J Organomet. Chem.* 1994, 480, C7–C9; Schumann, H. et al., *Chem. Ber.* 1994, 127, 2369–2372; Dias, H. V. R. et al., *Tetrahedron Lett.* 1994, 35, 1365–1366; Gridnev, A. A., et al., *Synth. Commun.* 1994, 24, 1547–1555; Herrmann, W. A., *Organometallics* 1995, 14, 1085–1086; Herrmann, W. A. et al., *Angew. Chem., Int. Ed. Engl.* 1995, 34, 2371–2374; Öfele, K. et al., *J Organomet. Chem.* 1995, 498, 1–14; Herrmann, W. A. et al., *J Organomet. Chem.* 1995, 501, C1–C4; Kuhn, N. et al., *Inorg. Chim. Acta* 1995, 238, 179–181; Herrmann, W. A. et al., *Chem. Eur. J* 1996, 2, 772–780; Herrmann, W. A. et al., *Chem. Eur. J* 1996, 2, 1627–1636; Herrmann, W. A. et al., *Angew. Chem., Int. Ed. Engl.* 1996, 35, 2805–2807; Herrmann, W. A. et al., *J Organomet. Chem.* 1996, 520, 231–234; Herrmann, W. A. et al., *Organometallics*, 1997, 16, 682–688; Herrmann, W. A. et al., *Organometallics* 1997, 16, 2209–2212; Herrmann, W. A. et al., *Organometallics* 1997, 16, 2472–2477; Herrmann, W. A. et al., *Angew. Chem., Int. Ed. Engl.* 1997, 36, 1049–1067; Herrmann, W. A. et al., *J Organomet. Chem.* 1997, 530, 259–262; Kocher, C. et al., *J Organomet. Chem.* 1997, 532, 261–265; Arduengo et al., *J. Am. Chem. Soc.*, 119: 12742 (1997); Hermann et al., *Angew. Chem. Int. Ed. Engl.*, 36, 2162 (1997); Köcher et al., *J. Organomet. Chem.*, 532: 26 (1997); Gardiner et al., *J. Organomet. Chem.*, 572: 239 (1999); *J. Organomet. Chem.*, 572: 177 (1999); Herrmann et al., *J. Organomet. Chem.*, 547: 357 (1997); Wang et al., *Organometallics* 17: 972 (1998); Liu et al., *Organometallics* 17: 993 (1998); Herrmann et al., *Organometallics* 17: 2162 (1998); Weskamp et al., *Angew. Chem. Int. Ed. Engl.* 37: 2490 (1998); Green et al., *J. Organomet. Chem.* 554: 175 (1998); Herrmann et al., *J. Organomet. Chem.* 557: 93 (1998); Arduengo et al., *Chemie Unserer Zeit* 32: 6 (1998); Voges et al., *Organometallics* 18: 529 (1999); Abernethy et al., *J. Am. Chem. Soc.* 121: 2329 (1999); Huang et al., *J. Am. Chem. Soc.* 121: 2624 (1999); Wang et al., *Organometallics* 18: 1216 (1999); McGuinness et al., *Organometallics* 18: 1596 (1999); WO97/34875 (Hoechst); EP-A-719753 (Hoechst); EP-A-719758 (Hoechst); DE-A-4447066 (Hoechst); and DE-A-4447070 (Hoechst).

Other suitable carbenes may be synthesised analogously.

Besides the unsaturated carbene ligands, ring saturated carbenes may also be used. Examples are described for example by Denk et al., in *Angew. Chem. Int. Ed. Engl.*, 36: 2607 (1997) and by Sellmann et al., in *J. Organomet. Chem.*, 541: 291 (1997).

Particularly suitable carbenes include: 1,3-dimethyl-imidazoline-2-ylidene, 1,3-di-i-propyl-imidazoline-2-ylidene, 1,3-di-n-butyl-imidazoline-2-ylidene, 1,3-di-t-butyl-imidazoline-2-ylidene, 1,3-di-trimethylsilyl-imidazoline-2-ylidene, 1,3-di-benzyl-imidazoline-2-ylidene, 1,3-di-cyclohexyl-imidazoline-2-ylidene, 1,3-diphenyl-imidazoline-2-ylidene, 1,3-bis(2,6-di-isopropyl)phenyl-imidazoline-2-ylidene, 1,3-bis(2,6-di-tertbutyl)phenyl-imidazoline-2-ylidene, 1,3-di-(1-naphthyl)-imidazoline-2-ylidene, 1,3-di-(anthracyl)-imidazoline-2-ylidene, 1-methyl-3-i-propyl-imidazoline-2-ylidene, 1-n-butyl-3-i-propyl-imidazoline-2-ylidene, 1-t-butyl-3-i-propyl-imidazoline-2-ylidene, 1-trimethylsilyl-3-i-propyl-imidazoline-2-ylidene, 1-benzyl-3-i-propyl-imidazoline-2-ylidene, 1-cyclohexyl-3-i-propyl-imidazoline-2-ylidene, 1-phenyl-3-i-propyl-imidazoline-2-ylidene, 1-bis(2,6-diisopropyl-phenyl)3-i-propyl-imidazoline-2-ylidene, 1-bis(2,6-ditertbutyl-phenyl)-3-i-propyl-imidazoline-2-ylidene, 1-mesityl-3-i-propyl-imidazoline-2-ylidene, 1-(1-naphthyl)-3-i-propyl-imidazoline-2-ylidene, 1-(1-anthracyl)-3-i-propyl-imidazoline-2-ylidene, 1-methyl-3-bis(2,6-diisopropyl-phenyl)-imidazoline-2-ylidene, 1-i-propyl-3-bis(2,6-diisopropyl-phenyl)-imidazoline-2-ylidene, 1-n-butyl-3-bis(2,6-diisopropyl-phenyl)-imidazoline-2-ylidene, 1-t-butyl-3-bis(2,6-diisopropyl-phenyl)-imidazoline-2-ylidene, 1-trimethylsilyl-3-bis(2,6-diisopropyl-phenyl)-imidazoline-2-ylidene, 1-benzyl-3-bis(2,6-diisopropyl-phenyl)-imidazoline-2-ylidene, 1-cyclohexyl-3-bis(2,6-diisopropyl-phenyl)-imidazoline-2-ylidene, 1-phenyl-3-bis(2,6-diisopropyl-phenyl)-imidazoline-2-ylidene, 1-bis(2,6-ditertbutyl-phenyl)-3-bis(2,6-diisopropyl)-phenyl)-imidazoline-2-ylidene, 1-mesityl-3-bis(2,6-diisopropyl-phenyl)-imidazoline-2-ylidene, 1-(1-naphthyl)-3-bis(2,6-diisopropyl-phenyl)-imidazoline-2-ylidene, 1-(1-anthracyl)-3-bis(2,6-diisopropyl-phenyl)-imidazoline-2-ylidene, 1-methyl-3-mesityl-imidazoline-2-ylidene, 1-i-propyl-3-mesityl-imidazoline-2-ylidene, 1-n-butyl-3-mesityl-imidazoline-2-ylidene, 1-t-butyl-3-mesityl-imidazoline-2-ylidene, 1-trimethylsilyl-3-mesityl-imidazoline-2-ylidene, 1-benzyl-3-mesityl-imidazoline-2-ylidene, 1-cyclohexyl-3-mesityl-imidazoline-2-ylidene, i-phenyl-3-mesityl-imidazoline-2-ylidene, 1-bis(2,6-diisopropyl-phenyl)-3-mesityl-imidazoline-2-ylidene, 1-bis(2,6-ditertbutyl-phenyl)-3-mesityl-imidazoline-2-ylidene, 1-(1-naphthyl)-3-mesityl-imidazoline-2-ylidene and 1-(1-anthracyl)-3-mesityl-imidazoline-2-ylidene.

The η-bonding ligand in the carbene-η-ligand complex used according to the invention may be any convenient mono or polycyclic ligand capable of η-bonding the catalytically effective metal using their η-orbitals, e.g. to form so-called "sandwich" or half sandwich complexes. η-bonding can thus be distinguished over bonding where only one atom of the ligand is bound to the metal, e.g. so-called sigma bonding. Typically the η-bonding ligand is a cyclopentadienyl ligand in which one or more of the ring carbons are optionally substituted, e.g. with halogen atoms or alkyl, aryl or aralkyl groups, or with fused rings, e.g. fused benzene or cyclohexene rings. Thus the η-ligand may be any of the η-ligands conventionally used in or proposed for metallocene catalysts. Moreover, if desired, the η-bonding ring may be coupled via a bridging group or directly to the carbene moiety.

Thus the cyclic carbene and η-ligand may conveniently comprise the following skeletal structure

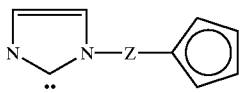

where Z is a bond or a one to three atom bridge, e.g. a bridge comprising carbon and/or silicon atoms. Such a bridge may conveniently be —CH₂—, CH₂CH₂ or Si(CH₃)₂. The ring atoms of this skeletal structure may conveniently be substituted, for example by pendant or fused ring substituents. Such substitution is desirably analogous to that described herein for the non-bridged cyclic carbene and η-ligands.

Bridged cyclic carbine/η-ligand ligands may be prepared by conjugating cyclic carbenes and η-ligands (or precursors therefor), preferably using difunctional bridging agents, e.g. alkylating or analogous agents (see Herrmann et al., *J. Organomet. Chem.* 547: 357 (1997)). By way of example the following schemes may be used to produce —CH₂— and —CH₂CH₂— bridged materials:

The η-bonding ligand may for example be of formula III $$CpY_m \qquad (III)$$

where Cp is an unsubstituted, mono-substituted or polysubstituted homo or heterocyclic cyclopentadienyl, indenyl, tetrahydroindenyl, fluorenyl, benzindenyl, cyclopenta[l] phenanthrenyl, azulenyl, or octahydrofluorenyl ligand; m is zero or an integer having a value of 1, 2, 3, 4 or 5; and where present each Y which may be the same or different is a substituent attached to the cyclopentadienyl ring moiety of Cp and selected from halogen atoms, and alkyl, alkenyl, aryl, aralkyl, alkoxy, alkylthio, alkylamino, (alkyl)₂P, alkylsilyloxy, alkylgermyloxy, acyl and acyloxy groups or one Y comprises an atom or group providing an atom chain comprising 1 to 4 atoms selected from C, O, S, N, Si and P, especially C and Si (e.g. an ethylene group) to a second unsubstituted, mono-substituted or polysubstituted homo or heterocyclic cyclopentadienyl, indenyl, tetrahydroindenyl, fluorenyl or octahydrofluorenyl ligand group.

In the η-bonding ligands of formula III, the non cyclopentadienyl rings may themselves be optionally substituted e.g. by halogen atoms or groups containing 1 to 10 carbon atoms.

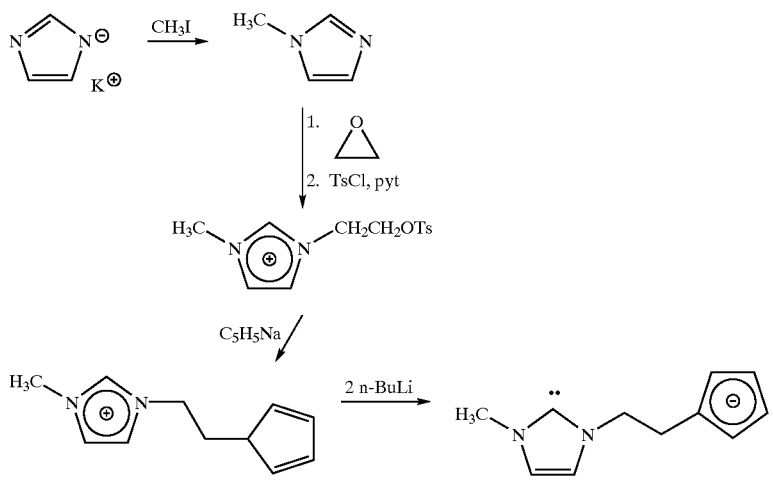

Scheme A

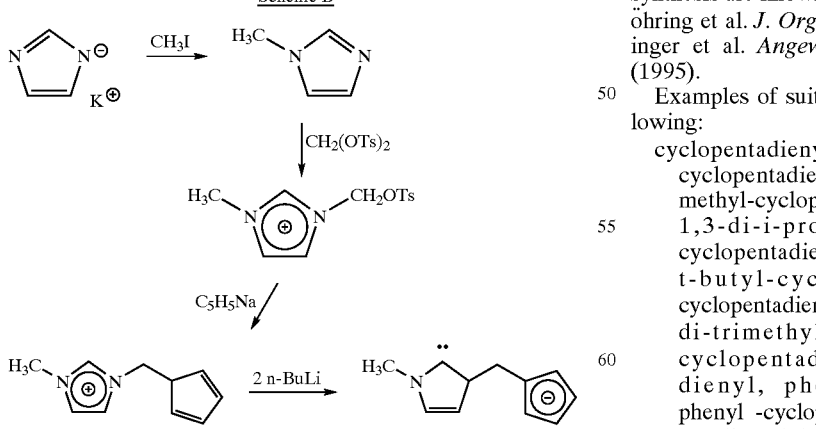

Scheme B

Bridged cyclic carbene/η-ligand liganded metals are preferably selected from groups 4 to 6 metals, especially Ti, Zr, Hf and Cr.

Many examples of each η-bonding ligands and their synthesis are known from the literature, see for example: M öhring et al. *J. Organomet. Chem* 479:1–29 (1994), Brintzinger et al. *Angew. Chem. Int. Ed. Engl.* 34:1143–1170 (1995).

Examples of suitable η-bonding ligands include the following:

cyclopentadienyl, indenyl, fluorenyl, pentamethyl-cyclopentadienyl, methyl-cyclopentadienyl, 1,3-di-methyl-cyclopentadienyl, i-propyl-cyclopentadienyl, 1,3-di-i-propyl-cyclopentadienyl, n-butyl-cyclopentadienyl, 1,3-di-n-butyl-cyclopentadienyl, t-butyl-cyclopentadienyl, 1,3-di-t-butyl-cyclopentadienyl, trimethylsilyl-cyclopentadienyl, 1,3-di-trimethylsilyl-cyclopentadienyl, benzyl-cyclopentadienyl, 1,3-di-benzyl-cyclopentadienyl, phenyl-cyclopentadienyl, 1,3-diphenyl -cyclopentadienyl, naphthyl-cyclopentadienyl, 1,3-di-naphthyl-cyclopentadienyl, 1-methyl-indenyl. 1,3,4-tri-methyl-cyclopentadienyl, 1-i-propyl-indenyl. 1,3,4-tri-i-propyl-cyclopentadienyl, 1-n-butyl-indenyl, 1,3,4-tri-n-butyl-cyclopentadienyl, 1-t-butyl-indenyl, 1,3,4-tri-t-butyl-cyclopentadienyl, 1-trimethylsilylindenyl, 1,3,4-tri-trimethylsilyl-cyclopentadienyl, 1-benzyl-indenyl, 1,3,4-tri-benzyl-cyclopentadienyl, 1-phenyl-indenyl, 1,3,4-tri-phenyl-cyclopentadienyl, 1-naphthyl-indenyl, 1,3,4-tri-naphthyl-cyclopentadienyl, 1,4-di-methyl-indenyl, 1,4-di-i-propyl-indenyl, 1,4-di-n-butyl-indenyl, 1,4-di-t-butyl-indenyl, 1,4-di-trimethylsilyl-indenyl, 1,4-di-benzyl-indenyl, 1,4-di-phenyl-indenyl, 1,4-di-naphthyl-indenyl, methyl-fluorenyl, i-propyl-fluorenyl, n-butyl-fluorenyl, t-butyl-fluorenyl, trimethylsilyl-fluorenyl, benzyl-fluorenyl, phenyl-fluorenyl, naphthyl-fluorenyl, 5,8-di-methyl-fluorenyl, 5,8-di-i-propyl-fluorenyl, 5,8-di-n-butyl-fluorenyl, 5,8-di-t-butyl-fluorenyl, 5,8-di-trimethylsilyl-fluorenyl, 5,8-di-benzyl-fluorenyl, 5,8-di-phenyl-fluorenyl and 5,8-di-naphthyl-fluorenyl.

Besides the carbene and η-bonding ligands, the carbene-η-ligand complex used according to the invention may include other ligands; typically these may be halide, hydride, alkyl, aryl, alkoxy, aryloxy, amide, carbamide or other two electron donor groups.

The carbene-η-ligand complexes used according to the invention may be produced relatively straight-forwardly by reacting a cyclopentadienyl-metal complex with a carbene or by reacting a metallocene with a salt, e.g. an imidazolium salt, of a protonated carbene. Sigma-bonded hydrocarbyl groups may subsequently be introduced for example by reaction with Grignard reagents. Such processes form further aspects of the present invention.

For use in olefin polymerization, the carbene-η-ligand complexes of the invention may be used together with a co-catalyst (or catalyst activator).

Thus viewed from a further aspect the invention provides an olefin polymerization catalyst system comprising (a) a cyclic carbene-η-ligand complex according to the invention and (b) a co-catalyst.

As a co-catalyst, an aluminoxane is preferred. Preferred aluminoxanes include $C_{1-10}$ alkyl aluminoxanes, in particular methyl aluminoxane (MAO). Such aluminoxanes may be used as the sole co-catalyst or alternatively may be used together with other co-catalysts. Thus besides or in addition to aluminoxanes other cation complex forming catalyst activators may be used. In this regard mention may be made of the silver and boron compounds known in the art. What is required of such activators is that they should react with the carbene-η-ligand complex to yield an organometallic cation and a non-coordinating anion (see for example the discussion on non-coordinating anions J in EP-A-617052 (Asahi)).

Aluminoxane co-catalysts are described by Hoechst in WO 94/28034. These are linear or cyclic oligomers having up to 40, preferably 3 to 20, $\text{-[Al(R'')O]-}$ repeat units (where R'' is hydrogen, $C_{1-10}$ alkyl (preferably methyl) or $C_{6-18}$ aryl or mixtures thereof).

In the polymerization process of the invention, more than one olefin monomers may be used. It is preferred that the comonomers be used in a minor amount, e.g. 0.5 to 40%, preferably 1 to 6% by weight, relative to the total monomer weight with the major monomer (e.g. ethene) making up the major amount, e.g. 60 to 99.5% by weight. Such comonomers may be other $C_{2-8}$ α-olefins but may also be more bulky monomers containing unsaturated carbon carbon bonds (especially C=C bonds) and, for example, up to 20 carbons, preferably up to 16 carbons, more preferably up to 14 carbons. Such comonomers may thus be mono or polycyclic, fused ring or unfused compounds containing one or more, e.g. 1, 2 or 3, unsaturated carbon carbon bonds. Examples of suitable such bulky comonomers include norbornene, norbornadiene and dicyclopentadiene. The use of the carbene-η-ligand catalysts of the invention is thus important in enabling the incorporation of such bulky comonomers within polyolefin products. Thus viewed from a further aspect the invention comprises a copolymer of a $C_{2-8}$ α-olefin and a mono or polycyclic monoene or polyene.

Viewed from a yet further aspect the invention provides a process for the catalysed polymerization of olefins, characterised in that as a catalyst is used a catalyst system according to the invention.

Viewed from a further aspect the invention provides a polymer article (e.g. a fibre, film or moulded article) formed from a polymer composition comprising a polymer produced by a process according to the invention, said composition optionally containing further components, e.g. further polymers, fillers, antioxidants, coloring agents, stabilizers (e.g. UV stabilizers), etc.

Polymerization according to the invention may be performed using standard polymerization techniques, e.g. gas phase, slurry phase or liquid phase polymerization and using conventional polymerization reactors, e.g. loop reactors, gas phase reactors, or stirred tank reactors, or combinations thereof.

Polymerization according to the invention may, as with conventional polymerizations, be effected in the presence of a solvent, e.g. an alkane (for example a $C_{3-7}$ alkane such as propane or n-butane), an aromatic compound (e.g. toluene) or a cycloaliphatic (e.g. cyclohexane).

The polymerization according to the invention is conveniently carried out in the temperature range of 0–300° C., more preferred from 60–120° C. Partial pressure range employed for the olefin(s) is conveniently from 1–2000 bars, more preferably from 5–20 bars.

It is particularly desirable that the carbene-η-ligand complex be supported on a solid substrate for use in such polymerization reactions. Such substrates are preferably porous particulates, e.g. inorganic oxides such as silica, alumina, silica-alumina or zirconia, inorganic halides such as magnesium chloride, or porous polymer particles, e.g. acrylate polymer particles or styrene-divinylbenzene polymer particles which optionally carry functional groups such as hydroxy, carboxyl etc. Particle sizes are preferably in the range 20 to 60 μm and porosities are preferably in the range 1 to 3 mL/mg. The complex may be loaded onto the support before or more preferably after it has been reacted with a co-catalyst. Desirably inorganic supports are heat treated (calcined) before being loaded with the complex.

While the catalytic metal in the carbene-η-ligand complexes used according to the invention is preferably a group 6 metal (e.g. Cr, Mo or W) and especially chromium, other catalytically effective transition or lanthanide metals can be used. Thus examples of the metal which may be coordinated in the carbene metallocene complex include group 3, 4, 5, 6, 7, 8, 9 and 10 metals, lanthanides and actinides. Particular metals which may be mentioned include Ti, Cr, Zr, Hf, V, Mn, Sc, Y, Nb, Ta, Re, Fe, Co, Ru, Os, Rh, Ir, Ni, Pd, Pt, Sm, Eu, La, Yb and Er.

The invention will now be described further with reference to the following non-limiting Examples.

GENERAL PROCEDURES

All manipulations involving organometallic compounds were carried out with use of vacuum line, Schlenk, syringe, or drybox techniques. Dichioromethane, dichloromethane-$d_2$, chioroform-d were distilled from $CaH_2$. THF was distilled from sodium benzophenone ketyl. $^1$H NMR spectra were recorded on Bruker DPX 200 and 300 instruments. Chemical shifts are reported in ppm relative to tetramethylsilane, with the residual solvent proton resonance as internal standards. Melting points were measured in capillary tubes sealed under vacuum. Solid state magnetic susceptibility study of CpCrCl (1,3-dimesitylimidazoline-2-ylidene) was conducted on a Quantum Design MPMS with a 5.5 Tesla super-conducting magnet and a SQUID detection system. Solution magnetic moments were measured by a modification of the Evan's method ($C_6D_5H$ as a reference) (see J. Chem. Soc. 2003–2005 (1959), J. Mag. Res. (1989) 169–173, and J. Chem. Educ. (1995) 39–40). EPR spectra were taken on a Bruker 200D-SRC instrument.

Polymerisations with ethylene were carried out either at atmospheric pressure in glass reactors or at 38 bar in a 1 litre autoclave. The polymerisations at atmospheric pressure were performed at 30° C. in toluene solution, while the high pressure polymerisations were carried out at 70 to 90° C. in isobutane slurry. In both reactors the pressure was maintained constant by continuously adding ethylene. In examples where either hydrogen, 1-hexene or norbornene was added, these were added prior to the polymerisation. Melt index (MI) and high load melt index (HLMI) were measured according to ASTM standard D1238 condition A and F respectively. Total methyl content was measured by infrared spectroscopy according to ASTM standard D2238–68, while the vinyl and transvinylene contents were determined as described by R. Blom et al. in J. Mol. Catal., 91 (1994) 237.

X-ray crystallography: Crystals were obtained by cooling a toluene/pentane solution at –35° C. A crystal (e.g. of dimensions 0.60×0.55×0.40 mm) was mounted on a glass fiber using paratone oil. X-ray data was collected on a Siemens SMART CCD diffractometer (Siemens Analytical X-ray Instruments Inc., Madison, Wis., USA) using graphite monochromated MoKα radiation. Data collection method: ω-scan, range 0.6°, crystal to detector distance 5 cm. Data reduction and cell determination were carried out with the SAINT and XPREP programs (Siemens Analytical X-ray Instruments Inc., Madison, Wis., USA). Absorption corrections were applied by the use of the SADABS program (Siemens Analytical X-ray Instruments Inc., Madison, Wis., USA). The structure was determined and refined using the SHELXTL program package (Siemens Analytical X-ray Instruments Inc., Madison, Wis., USA). The non-hydrogen atoms were refined with anisotropic thermal parameters; hydrogen positions were calculated from geometrical criteria and given isotropic thermal parameters.

Cp=cyclopentadienyl
Ph=phenyl
Cp*=pentamethylcyclopentadienyl

The publications referred to herein are hereby incorporated by reference.

EXAMPLE 1

Synthesis of 1,3-bis(2,4.6-trimethylphenyl) imidazolium Chloride

Synthesis of 1,3- bis(2,4,6-trimethylphenyl)-imidazolium choride followed a modification of the procedure given for 1,3-bis(4-methylphenyl)imidazolium choride in U.S. application Ser. No. 5,077,414. Trimethylaniline (13.5 g, 100 mmol), paraformaldehyde (1.50 g, 50 mmol) and toluene (40 mL) were combined in a round-bottom flask to make an orange slurry. Heating to 100° C. for 1 hour under inert atmosphere caused the mixture to become homogeneous.

After cooling to 40° C., concentrated HCl (37% in $H_2O$, 4.93 9, 50 mmol) was added, resulting in the immediate precipitation of copious amounts of white solid. To this suspension, glyoxal (40% in $H_2O$, 7.26 g, 50 mmol) was added which resulted in a color change to yellow. Afterwards, the mixture was heated to reflux for 1.5 hours during which it turned black. Cooling the mixture and removing the volatiles in vacuo left a sticky black tar. The substance was triturated and washed with acetone (15 mL). Upon filtration, 1,3-bis(2,4,6-trimethylphenyl)imidazolium choride was isolated as a pure (by $^1$H NMR) white solid in 40% yield.

EXAMPLE 2

Preparation of CpCrCl (1,3-dimesitylimidazoline-2-ylidene)

Solid 1,3-dimesitylimidazolium chloride (1.16 g, 3.40 mmol) was added to a dark solution of $Cp_2Cr$ (617 mg, 3.39 mmol) in THF (30 mL). After stirring for 1.5 hours, the resulting violet solution was filtered through a fine glass frit to remove dark insoluble impurities. The product was obtained as a violet powder (1.04 g, 67%) by addition of diethyl ether (30 mL) to the filtrate solution followed by overnight storage at –35° C.

hu 1H NMR ($C_6D6$, 200 MHz) δ 205 (br, $\omega_{1/2}$=2,800 Hz, 5H, Cp), 11.4 (br, (12=250 Hz, 4H, m-H), 7.2 (br, $\omega_{1/2}$=50 Hz, 6H, p-$CH_3$) 3.7 (br, $\omega_{1/2}$=790 Hz, 12H, o-$CH_3$), –4.4 (br, $\omega_{1/2}$=300 Hz, 2H, NCH). $\mu_{eff}$=4.62 $\mu_B$ (Evan's method). mp 248–254° C. no dec. Anal. Calcd for $C_{26}H_{29}ClCrN_2$: C, 68.34; H, 6.40; N, 6.13; Cr, 11.38. Found: C, 66.27; H, 6.33; N, 6.01; Cr, 11.50. MS (E.I): m/e 456 ($M^+$), 391 ($M^+$-Cp), 356 ($M^+$-Cp-Cl)

EXAMPLE 3

Preparation of CDCrPh(1,3-dimesitylimidazoline-2-ylidene)

Solid CpCrCl (1,3-dimesitylimidazoline-2-ylidene) (419.1 mg, 0.917 mmol) was dissolved in 20 ml THF. After the solution was cooled at –35° C., one equivalent of PhMgCl (0.510 mL, 1.8M) was added via syringe. The solution was observed to darken quickly and become brown. THF was removed under vacuum, and the brown solid residue was extracted with toluene (2×10 mL). A grayish, fine solid was removed when the toluene mixture was filtered through celite. Pentane (50 mL) was added to the solution causing the appearance of more fine powder. This too was removed by filtration through celite. Large, brown, x-ray quality, product crystals, in addition to smaller microcrystals, were observed to have formed upon cooling the solution at −35° C. overnight. Additional cooling resulted in the formation of additional product. The product was isolated by decanting the mother liquor (240 mg, 49%).

$^1$H NMR ($C_6D_6$, 200 MHz) δ 209 (br, $\omega_{1/2}$=3,660 Hz, 5H, Cp), 14.8 (br, $\omega_{1/2}$=210 Hz, 2H, Cr-Ph, m-H) 11.2 (br, $\omega_{1/2}$=255 Hz, 4H, mesityl, m-H), 7.96 (br, $\omega_{1/2}$=70 Hz, 6H, p-$CH_3$), 3.8 (br, $\omega_{1/2}$=1,100 Hz, 12H, o-$CH_3$), −6.5 (br, $\omega_{1/2}$=350 Hz, 2H, NCH), −111 (br, $\omega_{1/2}$=1,100 Hz, 1H, Cr-Ph, p-H), −164 (br, 6$\omega_{1/2}$=5,600 Hz, 2H, Cr-Ph, o-H). Anal. Calcd for $C_{32}H_{34}CrN_2$: C, 77.08; H, 6.87; N, 5.62. Found: C, 74.59; H, 6.79; N, 5.53. MS (E.I.): m/e 498 (M$^+$), 496 (M$^+$-2H), 421 (M$^+$-Ph), 420 (M$^+$-PhH), 356 (M$^+$-Ph-Cp).

EXAMPLE 4

Preparation of $CpCrCl_2$(1,3-dimesitylimidazoline-2-ylidene)

Method 1

A suspension of $CrCl_3(THF)_3$ in THF was added to equimolar amounts of NaCp to yield the known $CpCrCl_2$(THF). Equimolar amounts of the carbene 1,3-bis(2,4,6-trimethyl-phenyl)imidazolin-2-ylidene were added while stirring. The solvent was removed by vacuum transfer, and the residue was dissolved in toluene and filtered. The product was precipitated by concentrating the filtrate by vacuum transfer.

$^1$H NMR: δ 220 (br, Cp). UV/vis (THF, nm (e, m$^1$ cm,)) $\lambda_{max}$=685(470), 540(60). MS: m/e 491 (M$^+$).

Method 2

A solution of CpCrCl (1,3-dimesitylimidazoline-2-ylidene) in THF was cooled to −35° C. and an equimolar amount of $CCl_4$ was added. The solution quickly changed colour to become blue. The THF was removed under vacuum and the blue solid residue was extracted with toluene. The solution was filtered through celite and the title product was precipitated by the addition of pentane.

EXAMPLE 5

Preparation of CrCpPhCl (1,3-dimesitylimidazoline-2-ylidene)

Solid CrCpPh(1,3-dimesitylimidazoline-2-ylidene) (331.3 mg, 0.664 mmol) was dissolved in 10 mL THF and cooled to −35° C. To the cold solution was added an equimolar amount of $CCl_4$ (63.9 μL, in 2 mL of THF). The solution quickly changed colour and become red. The THF was removed under vacuum immediately after the colour change, and the red solid residue was extracted with toluene. The solution was filtered through celite and pentane was added to precipitate the title product (216.8 mg, 61%).

$^1$H NMR ($C_6D_6$, 200 MHz) δ 180 (br, $\omega_{1/2}$—Hz, 5H, Cp) 8.5 (br, $\omega_{1/2}$=200 Hz, 4H, mesityl, m-H), 5.8 (br, $\omega_{1/2}$=150 Hz, 6H, mesityl, p-$CH_3$), 3.8 (br, $\omega_{1/2}$=50 Hz, 12H, mesityl, o-$CH_3$), −5.4 (br, $\omega_{1/2}$=240 Hz, 2H, NCH). MS (E.I.): m/e 533 (M$^+$), 497 (M$^+$-HCl), 456 (M$^+$-Ph), 421 (M$^+$-ClPh).

EXAMPLE 6

Preparation of CrCpMe(1,3-dimesitylimidazoline-2-ylidene)

Solid CrCpCl (1,3-dimesitylimidazoline-2-ylidene) (420.0 mg, 0.919 mmol) was dissolved in 10 mL THF. After the solution was cooled to −35° C., one equivalent of MeMgCl (0.306 mL, 3.0 M) was added via syringe. The solution was observed to darken quickly and become brown. THF was removed under vacuum, and the brown solid residue was extracted with toluene and filtered through celite. Pentane was added to precipitate the title product (223.9 mg, 56%).

$^1$H NMR ($C_6D_6$, 200 MHz) δ 202 (br, $\omega_{1/2}$=2700 Hz, 5H, Cp), 11.5 (br, $\omega_{1/2}$=150 Hz, 4H, mesityl, m-H), 8.06 (br, $\omega_{1/2}$=60 Hz, 6H, mesityl, p-$CH_3$), 3.2 (br, $\omega_{1/2}$=—Hz, 12H, mesityl, o-$CH_3$), −4.11 (br, $\omega_{1/2}$=150 Hz, 2H, NCH)

EXAMPLE 7

Preparation of CrCpMeCl (1,3-dimesitylimidazoline-2-ylidene)

Solid CrCpMe(1,3-dimesitylimidazoline-2-ylidene) (203.4 mg, 0.465 mmol) was dissolved in 10 mL THF and cooled to −35° C. To the cold solution was added an equimolar amount of $CCl_4$ (44.8 μL, in 2 mL of THF). The solution quickly changed colour and become red. The THF was removed under vacuum immediately after the colour change, and the red solid residue was extracted with toluene. The solution was filtered through celite and pentane was added to precipitate the title product (198.5 mg, 90%).

$^1$H NMR ($C_6D_6$, 200 MHz) δ 168 (br, $\omega_{1/2}$=3,600 Hz, 5H, Cp), 8.7 (br, $\omega_{1/2}$=100 Hz, 6H, p-$CH_3$), 3.8 (br 12H, o-$CH_3$), −3.0 (br, $\omega_{1/2}$=350 Hz, 2H, NCH).

EXAMPLE 8

Preparation of CrCp($CH_2Si(CH3)_3$) (1,3-dimesitylimidazoline-2-ylidene)

Solid CrCpCl (1,3-dimesitylimidazoline-2-ylidene) (612.0 mg, 1.33 mmol) was dissolved in 10 mL THF. After the solution was cooled to −35° C., one equivalent of $(CH_3)_3SiCH_2Li$ (1.3 mL, 1.0 M) was added via syringe. The solution was observed to darken quickly and become brown. THF was removed under vacuum, and the brown solid residue was extracted with toluene and filtered through celite. Pentane was added to precipitate the title product (200.0 mg, 29%).

MS (E.I.): m/e 508 (M$^+$), 421 (M$^+$—$CH_2Si(CH_3)_3$). $^1$H NMR ($C_6D_6$, 200 MHz) δ 200 (br, $\omega_{1/2}$=3,500 Hz, 5H, Cp), 11.1 (br, $\omega_{1/2}$=350 Hz, 4H, mesityl, m-H), 7.73 (br, $\omega_{1/2}$=150 Hz, 6H, mesityl, p-$CH_3$), 3.4 (br, $\omega_{1/2}$=—Hz, 12H, mesityl, o-$CH_3$), −2.7 (br, $\omega_{1/2}$=400 Hz, 2H, NCH).

EXAMPLE 9

Preparation of CrCp)($CH_2Si(CH_3)_3$)Cl (1,3-dimesitylimidazoline-2-ylidene)

Solid CrCp($CH_2Si(CH_3)_3$) (1,3-dimesitylimidazoline-2-ylidene) (20 mg, 0.039 mmol) was dissolved in $CH_2Cl_2$ (2 mL). The solution changed colours immediately from brown to red. The solvent was removed under vacuum and the red solid residue extracted with pentane. Cooling of the pentane solution resulted in the formation of small product crystals.

$^1$H NMR ($C_6D_6$, 200 MHz) δ 168 (br, $\omega_{1/2}$=5,600 Hz, 5H, Cp), 8.6 (br, $\omega_{1/2}$=240 Hz, 6H, p-CH3), 3.8 (br 12H, o-$CH_3$), −3.0 (br, $\omega_{1/2}$=350 Hz, 2H, NCH).

EXAMPLE 10

Preparation of CD*CrCl (1,3-dimesitylimidazoline-2-ylidene)

Method 1

A solution of (Cp*CrCl)$_2$ was dissolved in THF and treated with equimolar amounts (on a per Cr basis) of a THF solution of the carbene 1,3-bis(2,4,6-trimethylphenyl)-imidazolin-2-ylidene. After 12 hours, the solvent was removed by vacuum transfer and the residue was dissolved in toluene and precipitated by concentration.

$^1$H NMR: δ 83 (br, Cp*). MS: m/e 526 (M$^+$).

Method 2

Solid {Cp*CrCl}$_2$ (70.7 mg, 0.159 mmol) was dissolved in THF (5 mL) and added to a solution of 1,3-dimesitylimidazoline-2-ylidene (89.4 mg, 0.293 mmol in 5 ml THF). After stirring for 24 hours, THF was removed under vacuum and a brown solid residue was extracted with toluene. After filtration, pentane was added to the solution to precipitate the title product. Brown flat crystals were formed. Yield 50 mg, 30%.

$^1$H NMR (C$_6$D$_6$ 200 MHz) δ 83.5 (br, ω$_{1/2}$=1,500 Hz, 5H, Cp*), 11.1 (br, ω$_{1/2}$=360 Hz, 4H, mesityl, m-H), 8.63 (br, ω$_{1/2}$=180 Hz, 6H, p-CH$_3$), 3.2 (br, ω$_{1/2}$=—Hz, 12H, mesityl, o-CH3), −1.9 (br, ω$_{1/2}$=400 Hz, 2H, NCH). MS (E.I.): m/e 526 (M$^+$), 490 (M$^+$-HCl), 391 (M$^+$-Cp*).

EXAMPLE 11

Preparation of Cp*CrCl$_2$(1,3-dimesitylimidazoline-2-ylidene)

A solution of (Cp*CrCl)$_2$ was dissolved in THF to yield the known Cp*CrCl$_2$(THF). Equimolar amounts of the carbene 1,3-bis(2,4,6-trimethylphenyl)-imidazolin-2-ylidene were added, and the solution was concentrated by vacuum transfer.

$^1$H NMR: δ −65 (br, Cp*).

EXAMPLE 12

Preparation of Solid Catalyst 2.0 g SiO$_2$ (EP10) calcined at 400° C. was added under argon atmosphere to a 100 ml round-neck-bottle. 10 ml toluene was added, then 6.45 ml MAO/toluene (7.4 wt % Al). This mixture was stirred for 0.5 hours. Then 35.11 mg (0.017 mmole) of CpCrCl (1,3-dimesitylimidazoline-2-ylidene) dissolved in 5 ml toluene was added by using a syringe (0.2 wt % Cr). The suspension turns blue. After another 0.5 hour reaction at ambient temperature, the solution is filtered and the solid product washed two times with 20 ml portions of pentane. The catalyst is then dried in vacuum and stored under argon. The colour of the final product is light yellow-green. Yield: 2.55 g.

EXAMPLE 13

Preparation of Solid Catalyst 13.1 mg CpCrCl (1,3-dimesitylimidazoline-2-ylidene) dissolved in 4.8 ml toluene was reacted with 4.8 ml of a toluene solution of MAO containing 7.4 wt % Al yielding a Al/Cr ratio of 400. After 15 minutes reaction time the resulting solution is added to 3.0 g silica which had been dehydroxylated at 400° C. After mixing, most of the toluene is removed,under reduced pressure yielding 4.35 g of catalyst.

EXAMPLE 14

Preparation of Solid Catalyst 3.5 ml of a toluene solution of MAO containing 7.4 wt % Al was added to 1.0 g silica that had been dehydroxylated at 400° C. After 30 minutes reaction time most of the toluene was removed under reduced pressure. Then 37 mg CpCrCl (1,3-dimesitylimidazoline-2-ylidene) dissolved in 3 ml toluene was added and the final mixture was stirred for 30 minutes before most of the toluene was removed under reduced pressure. The catalyst has a Al/Cr ratio of 100. Yield catalyst: 1.5 g.

EXAMPLE 15

Preparation of Solid Catalyst 1.0 g MgCl$_2$/SiO$_2$ (Sylopol 5550) was suspended in 8 ml toluene. Then 2.0 ml of a toluene solution containing 35 mg CpCrCl (1,3-dimesitylimidazoline-2-ylidene) was added while stirring. After 20 minutes reaction time most of the toluene was removed under reduced pressure yielding 1.2 g catalyst.

EXAMPLE 16

Preparation of Solid Catalyst 16.7 mg (3.6 10$^{-5}$ mole) CpCrCl (1,3-dimesitylimidazoline-2-ylidene) were reacted with 3.06 ml MAO/toluene (7.4 wt % Al). The reaction mixture was after 0.5 hr added to 0.95 g BE-059 (Poly (2-hydroxyethylmethacrylate-co-ethyleneglycol dimethacrylate), dried and washed) while stirring (incipient wetness). Most of the solvent is removed under reduced pressure. A prepolymerisation is then carried out to double the weight of the catalyst. Yield 2.17 g.

EXAMPLE 17

Polymerisation With CpCrCl (1,3-dimesitylimidazoline-2-ylidene)

To a glass reactor under argon atmosphere was added 50 ml of toluene. The argon was exchanged with ethylene and a toluene solution (2 ml) containing approximately 0.05 mmole CpCrCl (1,3-dimesitylimidazoline-2-ylidene) was added to the reactor. The chromium complex is lilac. Then 4.2 ml MAO/toluene (Al/Cr=100) is added. The solution turns olive and an ethylene flow of approximately 20 ml/min is observed over more than half an hour. Polymer yield after approximately 40 minutes: 0.98 g, corresponding to an activity of 565 gPE/(gCr.hr).

EXAMPLES 18–22

Polymerisations with Solid Catalyst

A series of polymerisations were carried out in a one litre autoclave using 0.5 l isobutane as diluent with the catalyst prepared in Example 12. The polymerisations were performed at different temperatures, with and without hydrogen and 1-hexene. The results are shown in Table 1.

TABLE 1

Results from polymerisations with
CpCrCl (1,3-dimesitylimidazoline-2-ylidene)/MAO/SiO$_2$
catalyst. 0.2 wt % Cr, Al/Cr = 200, between 0.3 and 0.4 g
catalyst was used in each run.

| Ex # | Poly. time | Temp °C. | D$_2$ bar | 1-hexene ml | Act. Kg/ (gCr.h) | HLMI | HLMI/MI | Density g/cm$^3$ | Me-tot/ 1000 C | Vinyl/ 1000 C |
|---|---|---|---|---|---|---|---|---|---|---|
| 18 | 65' | 80 | 0 | 0 | 18.5 | 255 | 165 | 0.970 | 3.4 | 4.4 |
| 19 | 100' | 80 | 1.0 | 0 | 6.6 | 19.5 | 250 | 0.959 | 2.7 | 2.6 |
| 20 | 85' | 80 | 0 | 10 | 6.7 | 0.57 | — | 0.970 | 2.7 | 1.8 |
| 21 | 122' | 90 | 0 | 0 | 24.1 | 430 | 146 | 0.963 | 3.9 | 5.1 |
| 22 | 187' | 70 | 0 | 0 | 8.1 | 14.5 | 403 | 0.965 | 3.8 | 4.8 |

EXAMPLE 23

Polymerisation with Solid Catalyst

Polymerisation with the catalyst described in Example 13 was carried out as described in Example 18. 0.3 g catalyst was used in the polymerisation. After 132 minutes polymerisation time, 18.7 g polyethylene was obtained, corresponding to an activity of 34.7 kgPE/(gCr.hr). HLMI was 7.8 and HLMI/MI was 600.

EXAMPLE 24

Polymerisation with Solid Catalyst

Polymerisation with the catalyst described in Example 14 was carried out as described in Example 18. 0.3 g catalyst was used in the polymerisation. After 300 minutes polymerisation time, 23.2 g polyethylene was obtained, corresponding to an activity of 3.4 kgPE/(gCr.hr). HLMI was 57.6 and HLMI/MI was 199.

EXAMPLES 25–27

Polymerisations with Solid Catalyst

The results from polymerisations with the catalyst described in Example 15 are given in Table 2 below.

TABLE 2

Polymerisations with four different
heterogenised catalysts based on CPCrCl
(1,3-dimesitylimidazoline-2-ylidene)/MgCl$_2$—SiO$_2$ catalysts.
All: 90° C., 38 bar total pressure.

| Ex # | Poly time | Carrier | wt % Cr | co-catalyst | Al Cr | Yield PE g | Activity kg Pe/g Cr.hr | Activity g$_{PE}$/g$_{cat}$ h | HLMI | HLMI/MI |
|---|---|---|---|---|---|---|---|---|---|---|
| 25 | 282' | MgCl$_2$—SiO$_2$ | 0.40 | DEAC† | 24 | 3.4 | 0.5 | 2.2 | — | — |
| 26 | 85' | MgCl$_2$—SiO$_2$ | 0.40 | MAO† | 400 | 76.0 | 48.7 | 178.8 | 28.5 | 285 |
| 27‡ | 270' | MgCl$_2$—SiO$_2$ | 0.40 | MAO† | 400 | 11.7 | 8.0 | 32.1 | 1.3 | — |

†Added to reactor, 0.300 g catalyst.
‡10 mL 1-hexene added, only 0.081 g catalyst, density 0.956

EXAMPLES 28–33

Polymerisation with Solid Catalyst

With the catalyst described in Example 16 a number of polymerisations were carried out at the conditions shown in Table 3.

TABLE 3

Polymerizations using heterogenised CpCrCl (1,3-dimesitylimidazoline-2-ylidene) MAO/polystyrene:divinyl benzene catalyst.
All: 90° C., 38 bar total pressure, $Al/C_1$ = 200, 0.2 wt % Cr.

| Ex # | Poly. time | Co-monomer | $p(H_2)$ bar | Yield PE | Activity kg PE/g Cr.h | Activity $g_{PE}/g_{cat}$.h | density g/cm$^3$ |
|---|---|---|---|---|---|---|---|
| 28 | 55' | — | — | 5.8 | 18 | 36 | — |
| 29 | 62' | — | — | 7.0 | 9 | 18 | 0.957 |
| 30 | 192' | 10 ml 1-hexene | — | 7.9 | 3 | 6 | 0.962 |
| 31 | 1080" | | 1.0 | 36.4 | 3 | 6 | 0.955 |
| 32 | 407' | 5 ml norbornene | — | 11.5 | 3 | 6 | — |
| 33 | 1200' | 5 ml norbornene | — | 8.9 | 1 | 2 | — |

*IR analyses give a total methyl content of 7.2, a vinyl content of 2.5 and a transvinylene content of 0.35. HLMI and HLMI/MI is 42.5 and 250, respectively.

What is claimed is:

1. A process for the catalysed polymerization of an olefin using as a catalyst or catalyst precursor a cyclic carbene-η-ligand complex comprising a catalytically effective coordinated group 4, 5 or 6 metal.

2. A process as claimed in claim 1 wherein said metal is a group 6 metal.

3. A process as claimed in claim 1 or 2 wherein said metal is chromium.

4. A process as claimed in claim 1 wherein said complex comprises a heterocyclic carbene ligand.

5. A process as claimed in claim 4 wherein said heterocyclic carbene ligand comprises a mono ring-unsaturated 5-ring membered heterocyclic ring containing 2, 3 or 4 ring nitrogens and an unsubstituted ring C: atom.

6. An olefin polymerization catalyst or catalyst precursor comprising a cyclic carbene-η-ligand complex comprising a catalytically effective coordinated group 4, 5 or 6 metal.

7. A catalyst or precursor as claimed in claim 6 wherein said complex comprises a heterocyclic carbene ligand.

8. A catalyst or precursor as claimed in claim 6 wherein the cyclic carbene ligand is of formula Ia or Ib (Ia)

$R^1{-}N{-}N{-}R^1$ with $X{=}X$ or (Ib)

$X{-}N{-}R^1$ / $X{-}N{-}R^1$ where each X may independently represent N or an optionally substituted CH group; and each $R^1$ is hydrogen, or an optionally substituted organic group.

9. A catalyst or precursor as claimed in claim 8 wherein said cyclic carbene ligand has a skeletal structure selected from the following:

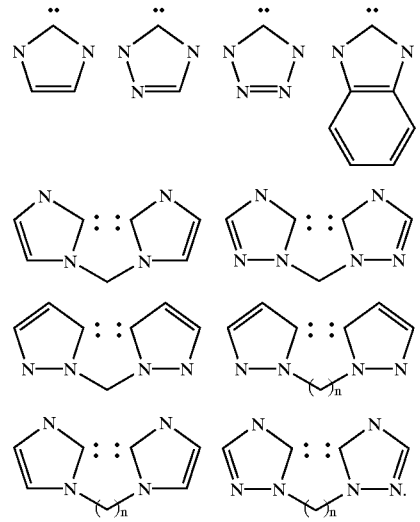

10. A catalyst or precursor as claimed in claim 8 wherein said cyclic carbene ligand is selected from the carbenes of formulae IIa to IIj

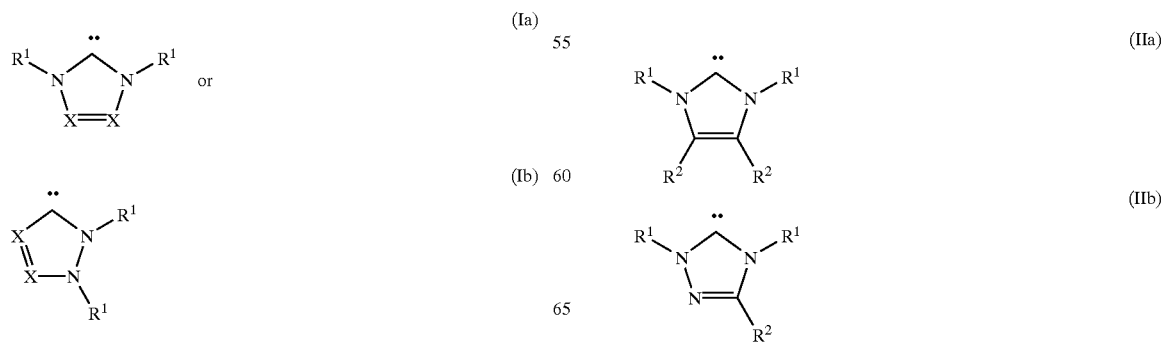

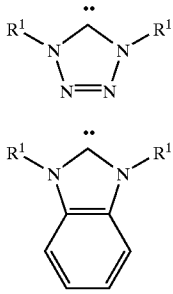 (IIc)

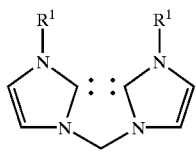 (IId)

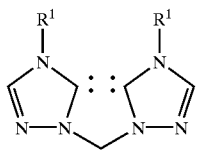 (IIe)

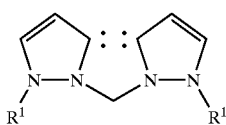 (IIf)

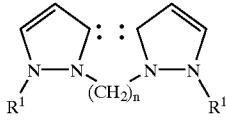 (IIg)

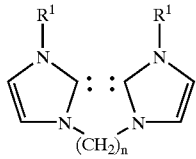 (IIh)

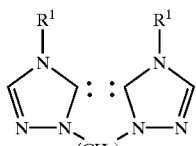 (IIi)

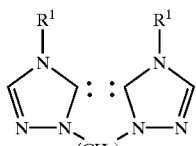 (IIj)

wherein n is from 1 to 6, and each $R^1$, which is the same or different, represents a $C_{1-6}$ alkyl group, a $C_{4-10}$ mono or polycyclic cycloalkyl group, a $C_{1-4}$ cycloalkyl-$C_{1-4}$ alkyl group, an aryl group, an aryl-$C_{1-4}$ alkyl group, a $C_{1-6}$ alkyl-aryl-$C_{1-4}$ alkyl group, or a carboxy group or derivative thereof, in which any alkyl, alkylene, aryl or arylene moiety is optionally substituted; and $R^2$ which may be the same or different is hydrogen, halogen, $C_{1-6}$ alkyl or an aryl group.

11. A catalyst or precursor as claimed in claim 6 wherein said cyclic carbene and said η-ligand are covalently attached to each other.

12. A catalyst or precursor as claimed in claim 11 wherein said cyclic carbene and η-ligand comprises the following skeletal structure

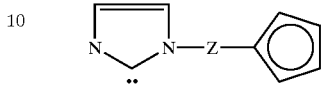

where Z is a bond or a one to three atom bridge.

13. A catalyst or precursor as claimed in claim 12 wherein Z comprises a carbon or silicon atom.

14. A catalyst or precursor as claimed in claim 6 wherein the η-ligand is of formula III $$CpY_m \qquad (III)$$

where Cp is an unsubstituted, mono-substituted or polysubstituted homo or heterocyclic cyclopentadienyl, indenyl, tetrahydroindenyl, fluorenyl, benzindenyl, cyclopenta[1]phenanthrenyl, azulenyl, or octahydrofluorenyl ligand; m is zero or an integer having a value of 1, 2, 3, 4 or 5; and where present each Y which may be the same or different is a substitutent attached to the cyclopentadienyl ring moiety of Cp and selected from halogen atoms, and alkyl, alkenyl, aryl, aralkyl, alkoxy, alkylthio, alkylamino, $(alkyl)_2P$, alkylsilyloxy, alkylgermyloxy, acyl and acyloxy groups or one Y comprises an atom or group providing an atom chain comprising 1 to 4 atoms selected from C, O, S, N, Si and P, to a second unsubstituted, mono-substituted or polysubstituted homo or heterocyclic cyclopentadienyl, indenyl, tetrahydroindenyl, fluorenyl or octahydrofluorenyl ligand group.

15. An olefin polymerization catalyst system comprising (a) a cyclic carbene-η-ligand complex as defined in claim 6 and (b) a co-catalyst.

16. A catalyst system as defined in claim 15, wherein said co-catalyst is an aluminoxane.

17. A catalyst or precursor as claimed in claim 6 further comprising a porous particulate support.

18. A process for the catalysed polymerization of olefins using as a catalyst a catalyst system as claimed in claim 15.

19. A polymer article formed from a polymer composition comprising a polymer produced by a process as claimed in claim 1.

20. A polymer obtainable by a process as claimed in claim 1.

21. A catalyst or precursor as claimed in claim 15 further comprising a porous particulate support.

22. A catalyst or precursor as claimed in claim 6, wherein the metal is a group 6 metal.

23. A catalyst or precursor as claimed in claim 22 wherein the metal is chromium.

* * * * *